United States Patent
Elson et al.

(10) Patent No.: US 6,336,902 B1
(45) Date of Patent: *Jan. 8, 2002

(54) SYSTEM FOR SENSING A CHARACTERISTIC OF FLUID FLOWING TO OR FROM A BODY

(75) Inventors: Edward E. Elson, Anaheim; Clement Lieber, Yorba Linda; Ronald L. McCartney, Orange; Wallace F. Cook, Yorba Linda, all of CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/475,606

(22) Filed: Jun. 7, 1995

Related U.S. Application Data

(63) Continuation of application No. 08/359,082, filed on Dec. 14, 1994, now abandoned, which is a continuation of application No. 08/193,672, filed on Feb. 7, 1994, now abandoned, which is a continuation of application No. 08/071,612, filed on Jun. 4, 1993, now abandoned, which is a continuation of application No. 07/780,051, filed on Oct. 21, 1991, now abandoned, which is a continuation of application No. 06/786,999, filed on Oct. 15, 1985, which is a continuation of application No. 06/741,396, filed on Jun. 5, 1985, now abandoned, which is a continuation of application No. 06/399,330, filed on Jul. 19, 1982, now abandoned.

(51) Int. Cl.[7] .................................. A61B 5/00
(52) U.S. Cl. ........................ 600/505; 600/526
(58) Field of Search ................ 128/637, 692, 128/713, 736; 604/901; 374/147–8, 158, 208–9

(56) References Cited

U.S. PATENT DOCUMENTS

| 3,545,428 A | * 12/1970 | Webster ................... 128/692 |
| 3,915,155 A | * 10/1975 | Jacobson et al. .......... 128/692 |
| 4,338,174 A | * 7/1982 | Tamura ................... 128/635 X |
| 4,476,877 A | * 10/1984 | Barker ................... 128/736 |

OTHER PUBLICATIONS

Barker Preliminary Motion Under 37 C.F.R. § 1.633(a) For Judgment (with Exhibits A, B and C).
Elson et al. Opposition to the Barker Preliminary Motion Under 37 C.F.R. § 1.633(a) For judgment Against Elson et al. (with Exhibits A and B and six Declarations).
Barker Reply Memorandum in Support of Its Preliminary Motion Under 37 C.F.R. § 1.633(a).
American Edwards laboratories internal memorandum from Eric Shore to Rod Carucci re: prototype hospital presentations.
Ellis et al., "Computerized monitoring of cardiac output by thermal dilution" *J. Assoc. Adv. Med. Instrum.*, Mar.–Apr. 1972, pp. 116–121.*#jf139##

*Primary Examiner*—Robert L. Nasser
(74) *Attorney, Agent, or Firm*—Rothwell, Figg, Ernst & Manbeck

(57) ABSTRACT

A system for sensing a characteristic of fluid flowing to or from the body of a human or animal comprising a conduit having a first end adapted to be outside the body, a second end adapted to be received within the body, and a flow passage through which fluid can flow between the first and second ends and a probe including a sensor for sensing a characteristic of the fluid. The probe is mounted on the conduit with the sensor in the flow passage. The sensor is isolated from the fluid flowing in the flow passage.

15 Claims, 3 Drawing Sheets

SYSTEM FOR SENSING A CHARACTERISTIC OF FLUID FLOWING TO OR FROM A BODY

This is a continuation of application Ser. No. 08/359,082, filed Dec. 14, 1994 now abandoned, which is a continuation of application Ser. No. 08/193,672, filed Feb. 7, 1994, now abandoned, which is a continuation of Ser. No. 08/071,612, filed Jun. 4, 1993, now abandoned, which is a continuation of Ser. No. 07/780,051, filed Oct. 21, 1991, now abandoned, which is a continuation of Ser. No. 06/786,999, filed Oct. 15, 1985, which is a continuation of Ser. No. 06/741,396, filed Jun. 5, 1985, now abandoned, which is a continuation of Ser. No. 06/399,330, filed Jul. 19, 1982, now abandoned.

BACKGROUND OF THE INVENTION

It is often necessary or desirable to measure the cardiac output of a patient. A common technique for accomplishing this is to inject a known volume of an injectate, such as a saline solution, into the right atrium. The injectate has a known temperature and it mixes with the blood to produce a temperature drop in the blood. The temperature of the blood is monitored at a suitable location downstream of the right atrium, and the data obtained can be used to determine cardiac output. This technique is commonly referred to as thermodilution, and the injection of the injectate and the downstream temperature measurement are carried out by a thermodilution catheter.

It is known to obtain the upstream temperature measurement of the injectate using a thermistor permanently mounted in the conduit which supplies the injectate. Although this system functions satisfactorily, it is necessary that the thermistor be initially sterile and be discarded after each usage. This increases the cost of using the thermodilution technique because the thermistor is a relatively expensive component. In addition, the thermistor bead material is subject to being attacked by the injectate.

The injectate may be at room temperature or at reduced temperatures. In the reduced temperature system, the injectate is cooled at one location and manually transported to the injection location near the proximal end of the thermodilution catheter. With this system, there is a risk of loss of sterility, the injectate may not be as cold as desired and there is an absence of a constant, ready supply of the injectate.

SUMMARY OF THE INVENTION

This invention provides for shielding the thermistor from the injectate and permits the thermistor to be reused even though other portions of the system may be disposable. This reduces the cost of the system, and the isolation of the thermistor from the injectate prevents the injectate from attacking the material of the thermistor bead. Furthermore, manual transport of the injectate is eliminated by providing a closed system in which a conduit carrier the cold injectate from a cooling container to the location where injection is to be carried out.

Although the concepts of this invention are particularly adapted for use in an injectate delivery system, in a broader sense, the concepts of the invention are also applicable to a system for sensing a characteristic of fluid flowing to or from the body of a human or animal. For example, the characteristic being sensed may be temperature, pressure or any characteristic that can be determined by an optical scan, such as the partial pressure of blood gases. This sensing can be carried out on any fluid, i.e., liquid or gas or mixture thereof, which is being injected into the body or being received from the body.

More particularly, the invention can be embodied in a system which includes a conduit having a first end adapted to be outside the body, a second end adapted to be received within the body and a flow passage through which fluid can flow between the first and second ends. The system also includes a probe, including means for sensing the desired characteristic of the fluid. Means is provided on the conduit for receiving at least the sensing means of the probe from the exterior of the conduit in the flow passage and isolating the probe from the fluid flowing through the flow passage. The probe can be mounted on the conduit with the sensing means in the flow passage and isolated from the fluid flowing in the flow passage so that the probe can sense the desired characteristic of the fluid in the conduit.

With this arrangement, the sensing means is isolated from the fluid flowing through the flow passage. For example, the sensing means may include a thermistor or fiber optics which can scan the fluid in the flow passage. Because the sensing means is isolated from the fluid in the flow passage, the probe need not be sterile. By removably mounting the probe on the conduit, at least the portion of the conduit having the receiving means can be disposed of without disposing of the probe.

The receiving means can be of various different constructions. For example, the receiving means may include a receiver projecting into the flow passage and having a receiver passage opening to the exterior of the flow passage for receiving the sensing means of the probe. Alternatively, the conduit may have a wall with a port leading to the fluid passage, and in this event, the receiving means may include a resilient membrane closing the port. The resilient membrane is deformable by the probe to permit at least the sensing means of the probe to be received in the flow passage.

The means for mounting the probe on the conduit preferably includes elongated telescoping members on the conduit and the probe, respectively. The telescoping members rigidly mount the probe and guide the sensing means into the receiving means.

When the system is used as an injectate delivery system, the conduit preferably has an inlet for receiving the injectate and an outlet through which the injectate can be delivered to the body. In this event, at least a downstream portion of the conduit includes a catheter for delivering the injectate to the interior of the body.

When the system is used to measure temperature, the projection of the receiving means into the flow passage creates turbulence adjacent the receiving means which assists heat transfer. To further increase heat transfer, the fluid passage can be restricted at the receiving means to increase the velocity of the injectate.

When using the system as a cold injectate system, the system preferably includes a cooling container, and the conduit leads from the receiving means to the cooling container with the cooling container being between the inlet and the receiving means. This provides a closed sterile system for the transfer of the cold injectate. In a preferred construction, the conduit includes several coils within the cooling container, and the storage volume within the cooling container is sufficient to store enough cold injectate for multiple injections. To reduce heat transfer to the injectate flowing from the cooling container, a length of the conduit downstream of the cooling container has a relatively low coefficient of heat transfer.

The injectate is forced through the conduit by a suitable pump, such as a syringe. By way of example, the conduit may include a first section coupled to the pump and extending past the receiving means and toward the outlet and an inlet section joined to the first section and leading to the inlet. A check valve is used for substantially preventing flow from the pump through the inlet section in a direction toward the inlet.

The invention, together with additional features and advantages thereof, may best be understood by reference to the following description taken in connection with the accompanying illustrative drawing.

BRIEF DESCRIPTION OF THE PREFERRED EMBODIMENT

Figure 1:
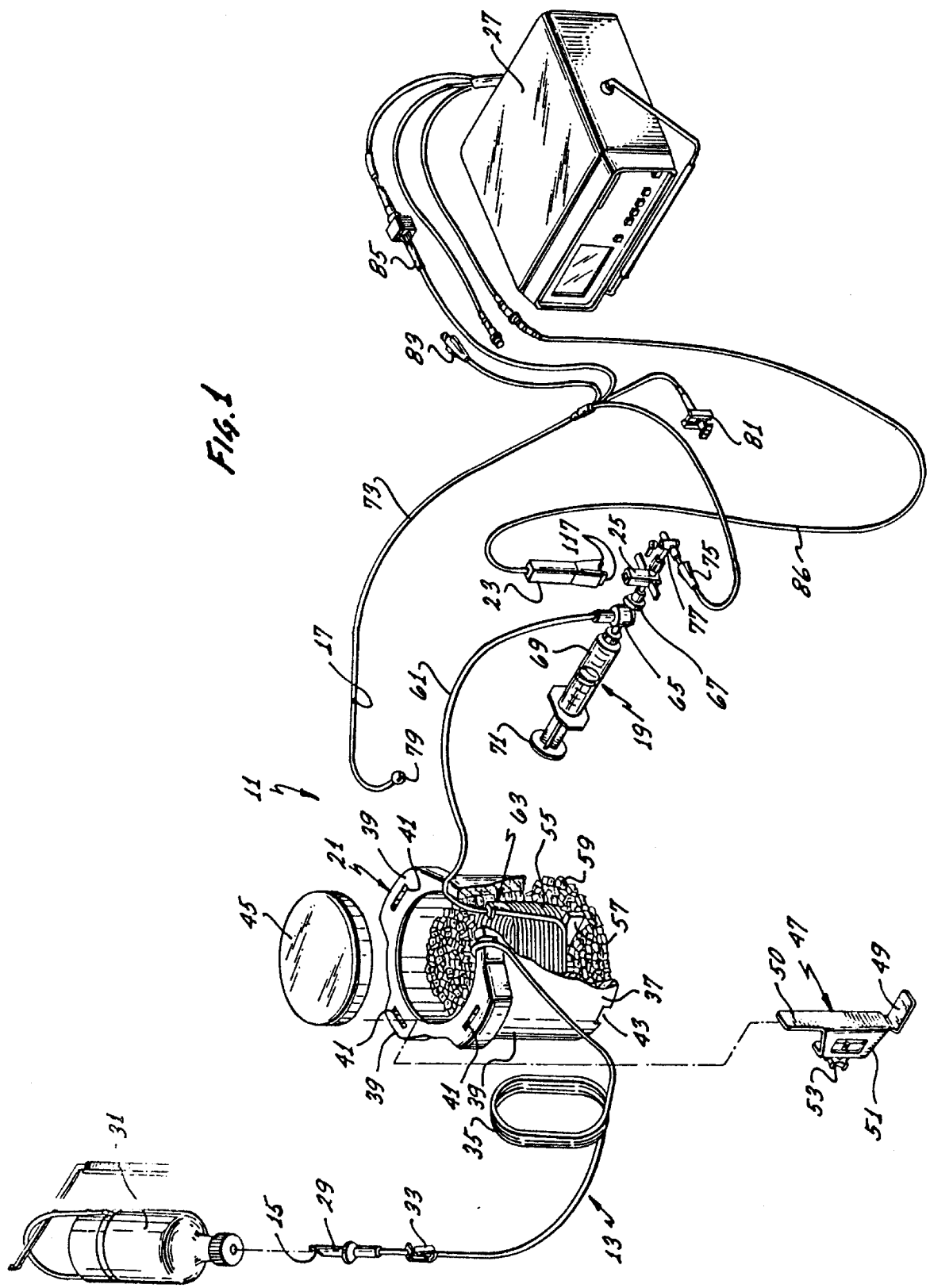
FIG. 1 is a perspective view of a system constructed in accordance with the teachings of this invention.

FIG. 1 shows a system 11 for sensing a characteristic of fluid flowing to or from the body of a human or animal. In the form shown in FIG. 1, the system is an injectate delivery system, and more specifically, the system 11 is adapted to measure cardiac output.

The system 11 includes a conduit 13 having an inlet 15 and an outlet 17, a pump in the form of a syringe 19, a cooling container 21, a probe 23 for making a temperature measurement, a flow-through fitting 25 adapted to cooperate with a probe 23 and a cardiac output computer 27. In the embodiment illustrated, the conduit 13 is comprised of various sections or components, and in the form shown, the inlet 15 is defined by an IV spike 29 which is adapted to penetrate a conventional bottle 31 of injectate so that the inlet 15 can receive the injectate from the bottle. For example, the injectate may be a saline solution.

A snap clamp 33 may be provided on the conduit 13 immediately downstream of the IV spike 29. A portion of the conduit 13 between the clamp 33 and the cooling container 21 is formed by a plurality of pull-apart coils 35. Conduit of this type comprises coiled tubing which tends to remain together in coiled form until the coils are pulled away. This provides a more compact system.

The use of the cooling container 21 is optional and would not be used, for example, if room temperature injectate were to be utilized. In the embodiment illustrated, the cooling container 21 comprises a container 37 having radially extending tabs 39 adjacent its upper end, slots 41 extending axially through the tabs, and a notch 43 at the lower end of the container. The upper end of the container 37 can be closed by a lid 45. The lid and the container 37 are preferably constructed of materials having a low coefficient of heat transfer.

The cooling container 21 can be supported on a horizontal surface or mounted on an IV pole by a bracket 47. The bracket 47 has a ledge 49 and a post 50 which can be received in the notch 43 and one of the slots 41, respectively.

The bracket 47 also has a pole mounting section 51 which can be slid onto an IV pole and retained in position on the pole by a screw 53.

A section of the conduit 13 is formed into coils 55 within the container 37, and the coils are elevated above the floor of the cooling container 21 by a partition 57. The coils 55 are constructed of thin-walled metal to provide good heat transfer, and the coils may be held together by a band (not shown). The container 37 may be filled with ice 59, water or other cold substance to reduce the temperature of the injectate within the coils 55. Preferably, the interior volume of the coils is sufficient to provide multiple injections of the injectate.

The conduit 13 also includes a section 61 of relatively low coefficient of heat transfer coupled to the coils 55 by an inline tubing connector 63. The section 61 extends downstream of the coils 55 to a check valve 65, and the latter is coupled to a fitting 67 to the flow-through fitting 25 and by an appropriate fitting to the syringe 19. The syringe 19 is of conventional construction and includes a housing 69 and a plunger 71 which can be withdrawn to draw injectate from the coils 55 through the check valve 65 and into the housing 69. Movement of the plunger 71 inwardly of the housing 69 expels the injectate through the downstream portions of the conduit 13 and out the outlet 17. During this time, the probe 23 is coupled to the flow-through fitting 25 to make a temperature measurement as described more particularly hereinbelow. The check valve 65 substantially prevents the injectate pumped by the syringe from flowing in the section 61 of the conduit back toward the inlet 15.

The downstream end of the flow-through fitting 25 is coupled to a conventional thermodilution catheter 73 which forms a portion of the conduit 13. More specifically, the catheter 73 has a proximal injectate hub 75 coupled to the downstream end of the flow-through fitting 25 by a fitting 77. The catheter 73 also includes a balloon 79, a balloon inflation valve 81 through which the balloon can be inflated and a distal lumen hub 83, a downstream thermistor (not shown) between the balloon 79 and the outlet 17 and a thermistor lead 85. The hub 83 is connectable to a suitable pressure monitor (not shown) for monitoring the pressure at the distal end of the catheter 73. For example, a thermodilution catheter of this type is available from American Edwards Laboratories, Santa Ana, Calif., as Model No. 93A-131-7F. The cardiac output computer 27 is coupled to the thermistor lead 85 and to leads 86 which are coupled to the probe 23.

In use, the catheter 73 is inserted, utilizing known techniques, into the heart and pulmonary artery with the outlet 17 being in the right atrium, and with the balloon being in the pulmonary artery. With the IV spike 29 coupled to the bottle 31, a ready supply of cold injectate is available in the coils 55. By moving the plunger 71 in a direction outwardly of the housing 69, a known amount of cold injectate can be drawn into the housing 69. By pushing the plunger 71 forwardly, this known volume of injectate is forced through the flow-through fitting 25, a length of the catheter 73 and the outlet 17 into the right atrium where it mixes with the blood and proceeds through the heart. The probe 23 measures the temperature of the injectate as it passes through the flow-through fitting 25, and the temperature of the blood-injectate mixture in the pulmonary artery is measured by the downstream thermistor adjacent the balloon 79. The cardiac output computer 27 processes this data in accordance with known techniques to ascertain cardiac output.

Figure 2:
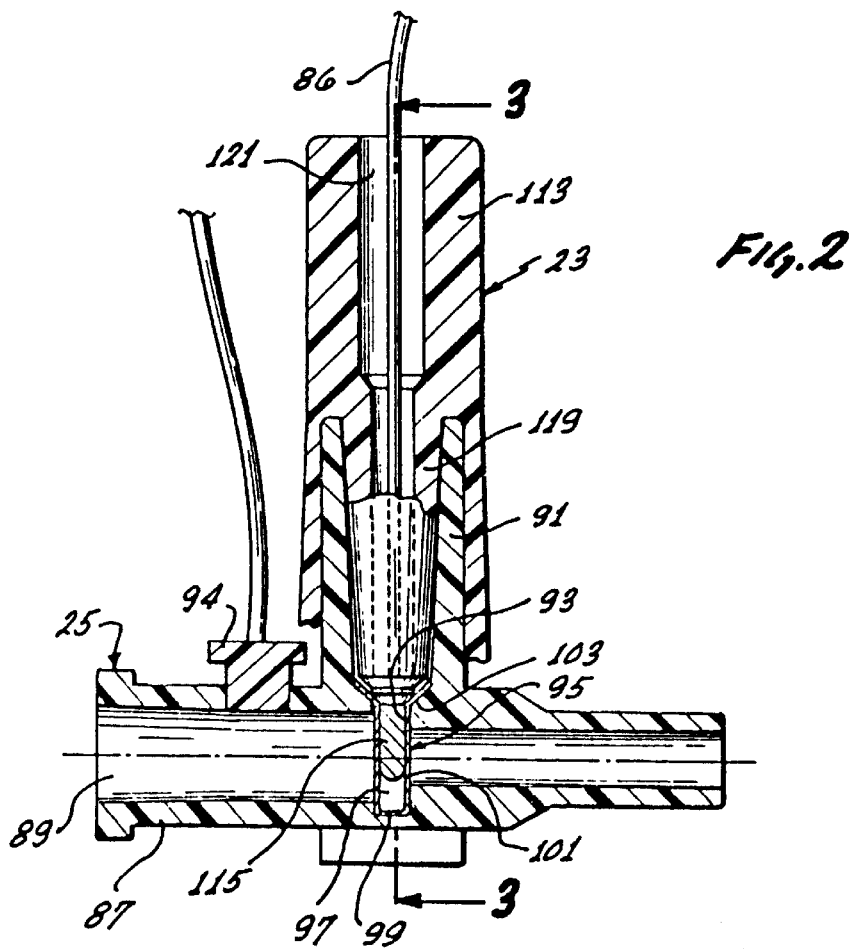
FIG. 2 is a longitudinal sectional view through the flow-through fitting and the probe.
Figure 3:
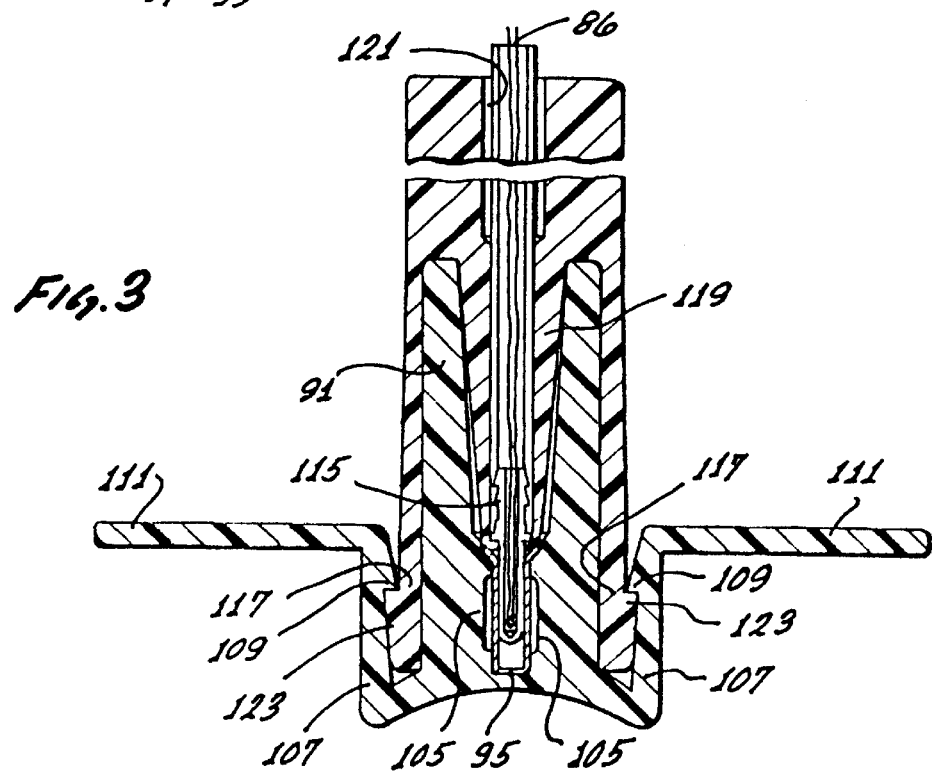
FIG. 3 is a sectional view taken generally along line 3—3 of FIG. 2.
Figure 4:
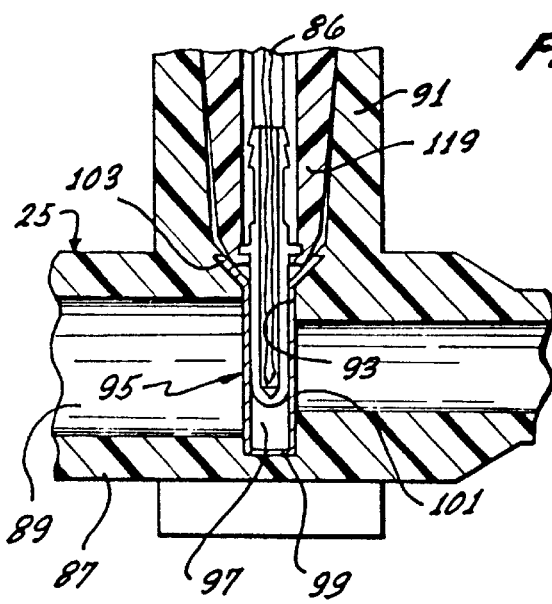
FIG. 4 is an enlarged fragmentary sectional view of a portion of FIG. 2.

FIGS. 2–4 show one preferred construction for the probe 23 and the flow-through fitting 25. The flow through fitting 25 which may be constructed of a suitable polymeric material, includes a tube section 87 which forms a portion of the conduit 13 and which has a passage 89 therein forming a portion of the flow passage of the conduit. An upstanding, elongated boss 91 is integrally joined to the tube section 87 and communication between the boss and the passage 89 is provided by a port 93 in the wall of the tube section. A pressure transducer 97 may, if desired, be mounted on the wall of the tube section 87.

A receiver 95 is mounted on the tube section 87 and extends diametrically completely across the passage 89. In this embodiment, the receiver 95 is a rigid, thin-wall, metal tube of high thermal conductivity that may be constructed, for example, of silver-plated copper. The receiver 95 has a receiver passage 97 which is sealed from the injectate in the passage 89. More specifically, the receiver 95 has an end wall 99 and a peripheral wall 101, both of which are imperforate and a flange 103 for assisting in sealing the receiver to the tube section 87. Although various methods of attachment may be used, in the embodiment illustrated, the receiver 95 is attached to the tube section 87 by insert molding. When so attached, the boss 91 and the receiver passage 97 are coaxial.

As best seen in FIG. 3, the flow-through fitting 25 includes a restriction 105 for restricting the flow passage 89 at the receiver 95. Also, for use in attaching the probe 23, the flow-through fitting 25 includes a pair of arms 107 with inwardly directed lugs 109 spaced outwardly from the boss 91. The arms 107 are sufficiently resilient so that the lugs 109 can be moved away from the boss 91 by pushing on ears 111 integrally joined to the arms 107, respectively.

The probe 23 includes a probe housing 113, which may be constructed of a suitable thermoplastic, and a thermistor 115. Although various constructions are possible, in the embodiment illustrated, the probe housing 113 has opposed mounting arms 117 adapted to telescopically receive the boss 91, and a tubular mounting section 119 in which the thermistor 115 is mounted. The probe housing 113 has an axial bore 121 through which the leads 86 extent and are coupled to the thermistor 115. The thermistor 115 projects from the outer end of the tubular mounting section 119 and is received within the receiver passage 97. The thermistor 115 may be pressed into the mounting section 119. The exterior of the probe housing 113 has outwardly projecting lugs 123 receivable beneath the lugs 109 to releasably mount the probe 23 on the flow-through fitting 25. When so mounted, the thermistor 115, which is of conventional construction, is housed within the receiver 95. The receiver 95 serves as an enclosure in which the thermistor 115 is sealed and isolated from the injectate in the passage 89.

Figure 6:
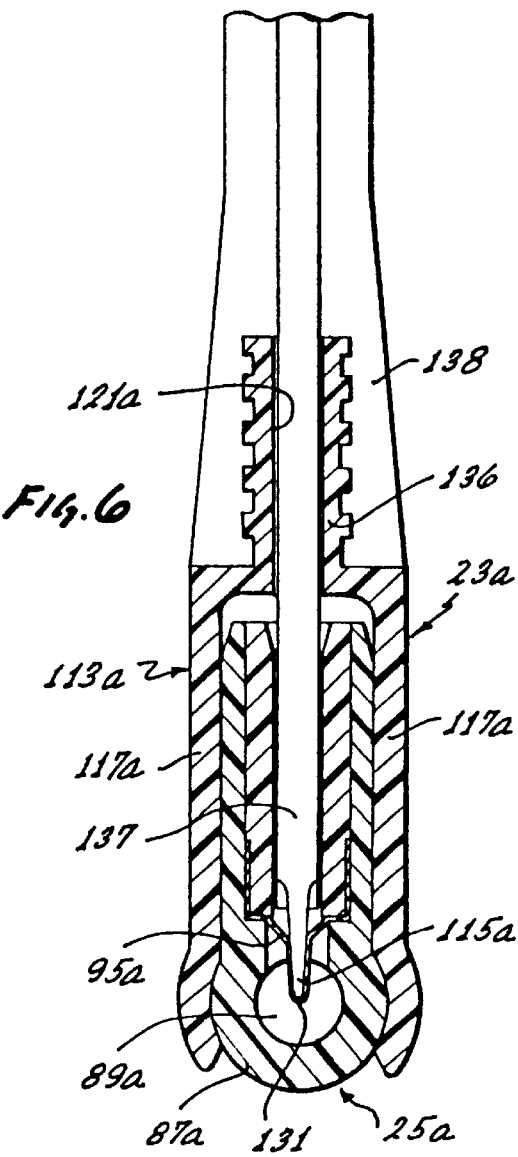
FIG. 6 is a sectional view of a probe and the flow-through fitting of FIG. 5 in the assembled condition.
Figure 5:
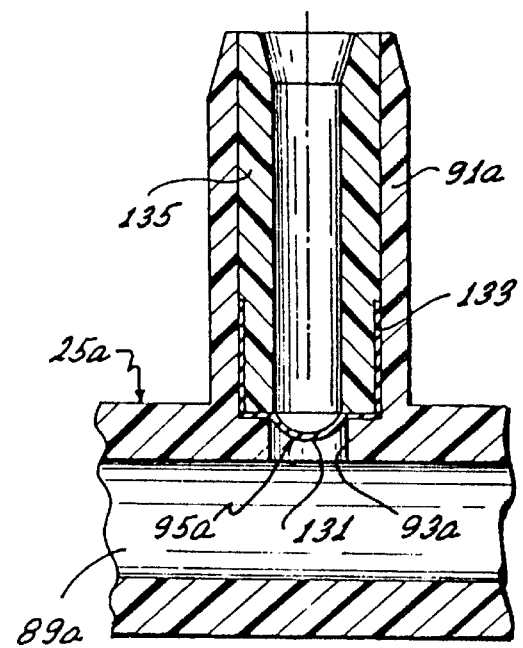
FIG. 5 is a fragmentary sectional view showing a second preferred form of the flow-through fitting.

FIGS. 5 and 6 show a second preferred form for the probe 23a and the flow-through fitting 25a. Portions of the probe 23a and fitting 25a corresponding to portions of the probe 23 and the fitting 25 are designated by corresponding reference numerals followed by the letter "a." The probe 23a and the fitting 25a are identical to the probe 23 and the fitting 25, respectively, in all respects not shown or described herein.

The primary difference between the fittings 25a and 25 is that the former has a receiver 95a in the form of a thin, resilient membrane of a suitable rubber. The receiver 95a in the form illustrated is in the form of a sock having an imperforate end wall 131 and a peripheral wall 133 with the latter being firmly held between the boss 91a and a tubular insert 135 which is suitably mounted within the boss.

The probe housing 113a includes a rigid section 136 and a pliable section 138. The probe housing is removably attached to the fitting 25a by resilient arms 117a which partially embrance the tube section 87a. The thermistor 115a is mounted on a support 137 of plastic or other suitable material, and the support 137 is suitably mounted on a mounting section 139 of the probe housing 113a.

With the probe 23a detached from the fitting 25a, the end wall 131 lies in the port 93a out of the passage 89a. However, when the probe 23a is mounted on the fitting 25a as shown in FIG. 6, the end of the thermistor 115a engages the end wall 131 and resiliently deforms it to permit the thermistor to project a substantial distance into the passage 89a. In this position, the thermistor 115a is isolated and sealed from the injectate in the passage 89a by the membrane-like receiver 95a. The membrane can be extremely thin so that it is a very effective heat transfer member which enables the thermistor 115a to provide a very accurate temperature reading.

Although exemplary embodiments of the invention have been shown and described, many changes, modifications and substitutions may be made by one having ordinary skill in the art without necessarily departing from the spirit and scope of this invention.

What is claimed is:

1. In a cardiovascular flow measuring system comprising means for providing a cold injectate fluid from a supply of said cold injectate fluid, a conduit through which said cold injectate fluid is delivered in a known amount from said supply into a patient's blood vessel, means for sensing a resultant change in the temperature of the patient's blood, said means for sensing comprising a temperature sensor, and means for determining the circulatory blood flow rate, the improvement which comprises:

a disposable housing defining a through lumen for conducting injectate fluid therethrough;

a disposable thermally conductive enclosure hermetically sealingly joined to the housing and projecting transversely into said lumen to be in heat transfer association with injectate fluid conducted through said lumen; and a reusable temperature sensor removably installed in said enclosure, said sensor providing a signal corresponding accurately to the temperature of the injectate fluid conducted through said lumen.

2. The cardiovascular flow measuring system of claim 1 wherein said enclosure projects substantially across said lumen.

3. The cardiovascular flow measuring system of claim 2 wherein said enclosure has a resilient end wall and said enclosure projects substantially across said lumen by said reusable temperature sensor engaging said end wall and resiliently deforming it.

4. The cardiovascular flow measuring system of claim 1 wherein said enclosure is relatively rigid and projects substantially across said lumen at all times.

5. The cardiovascular flow measuring system of claim 4 wherein said enclosure is constructed of a metal and is of high thermal conductivity.

6. The cardiovascular flow measuring system of claim 1 wherein said reusable temperature sensor is included in a probe.

7. The cardiovascular flow measuring system of claim 1 wherein said reusable temperature sensor is a thermistor.

8. The cardiovascular flow measuring system of claim 1 wherein said reusable temperature sensor is fiber optics.

9. The cardiovascular flow measuring system of claim 1 wherein said enclosure projects fully across said lumen.

10. The cardiovascular flow measuring system of claim 1 wherein a thermodilution catheter forms a portion of the conduit and is coupled to said disposable housing by a fitting.

11. The cardiovascular flow measuring system of claim 1 wherein said enclosure is constructed of a metal and is of a high thermal conductivity whereby said reusable temperature sensor when installed in said enclosure is highly responsive to temperature changes in said injectate fluid.

12. The cardiovascular flow measuring system of claim 1 wherein said enclosure has a high thermal conductivity over substantially the entire portion of said enclosure that projects transversely into said lumen.

13. The cardiovascular flow measuring system of claim 1 wherein said enclosure has a resilient end wall which is of a high thermal conductivity whereby said reusable temperature sensor when installed in said enclosure is highly responsive to temperature changes in said injectate.

14. The cardiovascular flow measuring system of claim 13 wherein said end wall is resiliently deformable membrane.

15. The cardiovascular flow measuring system of claim 1 wherein said disposable housing comprises inner walls which are shaped to restrict flow of said injectate fluid at said enclosure whereby the velocity of said injectate fluid at said enclosure is increased to improve heat transfer through said enclosure.

* * * * *